US007682365B2

(12) United States Patent
Guinan

(10) Patent No.: US 7,682,365 B2
(45) Date of Patent: Mar. 23, 2010

(54) CATHETER DEVICE FOR SUPPORT OF A GUIDEWIRE IN CROSSING A LESION

(75) Inventor: Terry Guinan, Loughrea (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 590 days.

(21) Appl. No.: 11/559,043

(22) Filed: Nov. 13, 2006

(65) Prior Publication Data
US 2008/0114390 A1 May 15, 2008

(51) Int. Cl.
*A61F 11/00* (2006.01)
(52) U.S. Cl. ..................................... 606/108
(58) Field of Classification Search ................. 606/108; 600/585
See application file for complete search history.

(56) References Cited

U.S. PATENT DOCUMENTS

| | | | |
|---|---|---|---|
| 4,699,611 A | 10/1987 | Bowden | |
| 4,932,959 A * | 6/1990 | Horzewski et al. | 606/194 |
| 5,265,622 A | 11/1993 | Barbere | |
| 6,168,571 B1 | 1/2001 | Solar et al. | |
| 6,270,465 B1 | 8/2001 | Keith et al. | |
| 6,916,293 B2 * | 7/2005 | Hamilton | 600/585 |
| 7,217,264 B2 * | 5/2007 | Gobron et al. | 606/1 |
| 2004/0030290 A1 | 2/2004 | Mangano et al. | |
| 2004/0127847 A1 * | 7/2004 | DuBois et al. | 604/95.04 |

* cited by examiner

*Primary Examiner*—Todd E Manahan
*Assistant Examiner*—Kevin Everage

(57) ABSTRACT

A catheter device selectively provides additional support to a guidewire for aiding the guidewire in crossing a narrowing in a body lumen. The catheter device includes an elongate outer tubular member having a tapered distal end. An elongate guidewire gripping member is slidably disposed within the outer tubular member. The guidewire gripping member has a lumen for slidably receiving the guidewire and a distal end having a plurality of longitudinal fingers. When the guidewire gripping member is advanced distally against the tapered distal end of the outer tubular member, a the fingers of the guidewire gripping member are forced to engage with the guidewire to thereby prevent movement of the guidewire relative to the catheter device. The catheter device may include a steering mechanism for steering the combined catheter device and guidewire component to an optimum starting point for crossing the lesion.

21 Claims, 4 Drawing Sheets

CATHETER DEVICE FOR SUPPORT OF A GUIDEWIRE IN CROSSING A LESION

FIELD OF THE INVENTION

The invention relates generally to an intra-luminal device for use in crossing a norrowing in a body passageway. More particularly, the invention relates to a catheter device that selectively provides additional stiffness and support to a guidewire for crossing a chronic total occlusion (CTO) in a blood vessel.

BACKGROUND OF THE INVENTION

Stenotic lesions may comprise a hard, calcified substance and/or a softer thrombus material, each of which forms on and within the lumen walls of a blood vessel and restricts blood flow through the lumen. Intra-luminal treatments such as balloon angioplasty (PTA, PTCA, etc,)) stent deployment, atherectomy, and thrombectomy are well known and have proven effective in the treatment of such stenotic lesions. These treatments often involve the insertion of at therapy catheter into a patient's vasculature, which may be tortuous and may have numerous stenoses of varying degrees throughout its length. In order to place the distal end of a catheter at the treatment site, a guidewire is typically introduced and tracked from an incision, through the vasculature, and across the lesion. Then at catheter (e,g., a balloon catheter), perhaps carrying a stent at its distal end, can be tracked over the guidewire to the treatment site. Ordinarily, the distal end of the guidewire is quite flexible so that it can be rotatably steered and pushed through the bifurcations and turns of the typically irregular passageway without damaging the vessel walls.

In some instances, the extent of occlusion of the lumen is so severe that the lumen is completely or nearly completely obstructed, which may be described as a total occluslon. If this occlusion persists for a long period of time, the lesion is referred to as a chronic total occlusion or CTO. Furthermore in the case of diseased blood vessels, the lining of the vessels may be characterized by the prevalence of atheromatous plaque which may form total occusions. The extensive plaque formation of a chronic total occlusion typically has a fibrous cap surrounding softer plaque material. This fibrout cap tray present a surface that is difficult to penetrate with a conventional guidewire, and the typically flexible distal tip of the guidewire may be unable to cross the lesion.

Thus for treatment of total occlusions, stiffer guidewires have been employed to recanalize through the total occlusion. However due to the fibrous cap of thee total occlusion, a stiffer guidewire still may not be able to cross the occlusion. Further, in a CTO there may be a distortion of the regular vascular architecture, such that there may be multiple small non-functional channels throughout the occlusion rather than one central lumen for recanalizaition. Furthermore these spontaneously recanalized channel may be responsible for failers due to their dead-end pathways, which may misdirect the guidewires. Once a "false" tract is created by a guidewire, subsequently attempts to cross the CTO with different guidewires may continue to follow the same incorrect path as it is very difficult to steer subsequent guidewire away from the false tract.

What is needed is a steerable device that aids in directing a guidewire to an optimum approach for crossing a chronic total occlusion CTO, as well as provides support to the guidewire for pushing the guidewire through the CTO.

BRIEF SUMMARY OF THE INVENTION

Accordingly, disclosed herein is a catheter device that provides additional support to a guidewire for aiding the guidewire in crossing a lesion in a body lumen. The catheter device includes a elongate outer tubular member with a lumen that extends from a proximal end to a distal end thereof. The outer tubular member has a distal end with a tapered portion. The catheter device further includes a guidewire gripping member that is slidably disposed in the lumel of the outer tubal member. The guidewire gripping member has a guidewire lumen for slidably receiving the guidewire and a distal end with a plurality of longitudinal slots defining gripping jaws therein. When the guidewire gripping member is advanced distally within the outer tubular members, the gripping contact the tapered portion of the outer shaft, such that or fingers of the guidewire gripping member to forced to grip with the guidewire to thereby prevent movement of the guidewire relative to the catheter device.

In an embodiment the catheter device includes a steering wire for deflecting a distal end of the catheter device. In a further embodiment, a hub is disposed at a proximal end of the catheter device includes one or more actuation mechanism for advancing and retracting the guidewire gripping member and/or the steering wire within the outer tubular member.

A method of crossing a lesion in a body lumen in accordance with another embodiment of the present invention includes advancing a guidewire through a patient's vasculature to position a distal end of the guidewire proximate to the lesion. A catheter device is then provided that includes an elongate outer shaft with a tapered distal portion and a guidewire gripping member slidably disposed within the outer shaft, wherein the guidewire gripping member includes a guidewire lumen and a longitudinally slotted distal end having gripping jaws or fingers. The catheter device is tracked over the guidewire until distal end of the catheter device is positioned proximate to the distal end of the guidewire. The method further includes engaging the catheter device with the guidewire by distally advancing the guidewire gripping member relative to the outer shaft of the catheter device such that the interactin between the gripping fingers at the distal end of the guidewire gripping member and the tappered distal portion of the outer shaft secures the catheter device to the guidewire. The combined catheter device and guidewire component are then distally pushed through the lesion.

In a method in accordance with another embodiment, the catheter device further includes a steering, wire attached to the distal end of the catheter device, wherein prior to the step of distally advancing the guidewire gripping member relative to the outer shaft of the catheter device, the steering wire is retracted to deflect the distal end of the catheter device so that the combined catheter device and guidewire component may be steered to optimum crossing point in the lesion, prior to the step of pushing the combined catheter device and guidewire component through the lesson.

BRIEF DESCRIPTION OF THE DRAWINGS

The foregoing and other features and advantages of the invention will be aparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described figures, wherein like reference numbers indicate identical or functionally similar elements. The terms "distal" and "proximal" are used in the following description with respect to a position or direction relative to the treating clinican. "Distal" and "distally" are a position distant from or in a direction away from the clinician. "Proximal" and "proximally" are a position near or in a direction toward the clinician.

The present invention is a catheter device for use in conjunction with a guidewire for crossing total occlusion or a chronic total occlusion (CTO). However, it will be understood that the invention is not limited to treatment of CTOs, or to treatment of blood vessels, for that matter. The invention may be useful wherever a clinician encouters difficulty navigating a medical guidewire across a narrowing in a body passageway. The catheter device acts as a catheter providing the guidewire with additional support. The catheter device may selectively secured to the guidewire to allow the guidewire to be pushed into a through the lesion, i.e., the total occlusion or CTO. In various embodiments, the catheter device may be steerable to position the guidewire at an optimal starting point for crossing the CTO.

Figure 1:
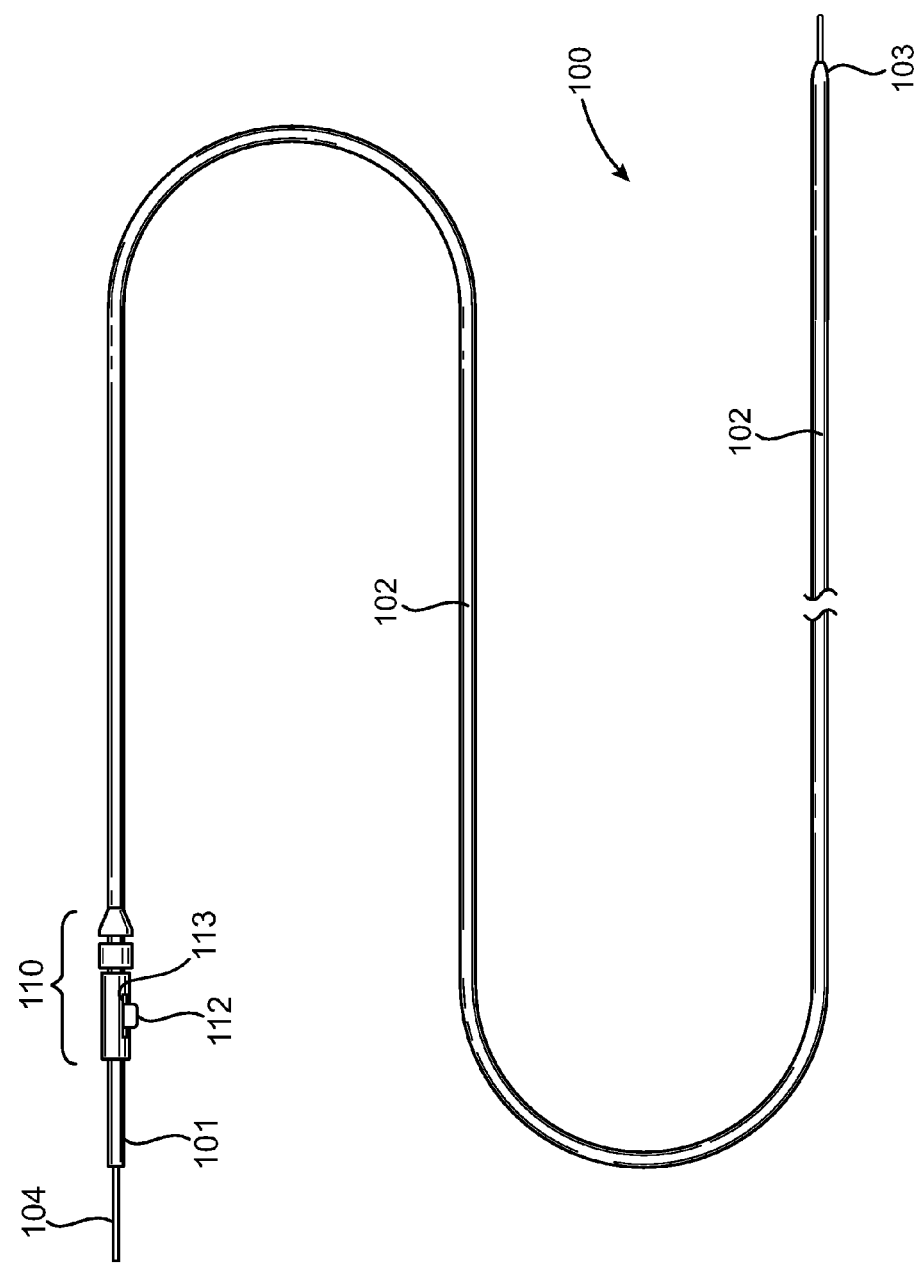
FIG. 1 illustrates a side view of a catheter device in accordance with an embodiment of the present invention.
Figure 2:
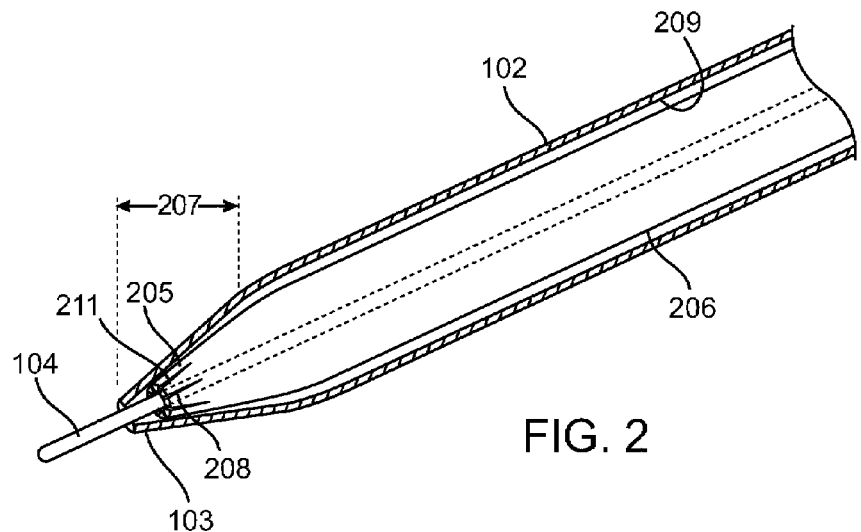
FIG. 2 illustrates a partial longitudinal sectional view of a distal portion of the catheter device of FIG. 1.

As illustrated with reference to FIGS. 1 and 2, catheter or catheter device 100 includes an elongate tubular member, or outer shaft 102 having a proximal end 101, a distal end 103 and a full-length lumen 209. A guidewire gripping member 206, which in this embodiment is an elongate tubular member or inner shaft, is slidably disposed within outer shaft lumen 209 from a hub 110 to a tapered portion 207 adjacent distal end 103 of outer shaft distal end 103. In tapered portion 207, at least the inside diameter of outer shaft 102 becomes narrower as it approaches distal end 103. As illustrated, in tapered portion 207, the outer diameter of outer shaft 102 may also become narrower as it approached distal end 103. The wall thickness in tapered portion 207 may be uniform or varied.

Hub 110 includes an actuation button 112 for slidably advancing and retracting guidewire gripping member 206 within outer shaft 102. Actuation button 112 is slidable within an actuation slot 113, which in an embodiment, limits how far distally guidewire gripping member 206 may be advanced. Other types of control mechanisms are possible for slidably advancing and retracting guidewire gripping member 206 within outer shaft 102, as will be understood by those of ordinary skill in the art.

Figure 3:
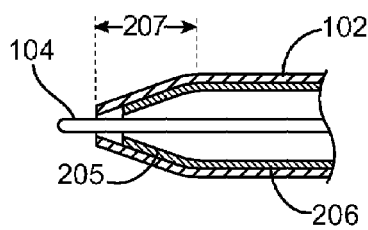
FIGS. 3 and 4 illustrate longitudinal sectional views of a distalmost portion of the catheter device of FIG. 1 in an engaged and unengaged configuration, respectively.
Figure 4:
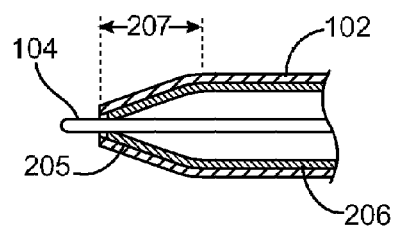

A conventional guidewire 104 removably and slidably extends through a lumen within guidewire gripping member 206. Catheter device 100 is trackable over and selectively securable to guidewire 104 depending on the position of a distal end 205 of guidewire gripping member 206 within outer shaft 102. A plurality of slots 208 extend longitudinally from distal end 205 of guidewire gripping member 206 to define a plurality of flexible, gripping jaws or fingers 211. When distal end 205 is advanced within tapered portion 207 of outer shaft 102, slots 208 between fingers 211 allow fingers 211 to converge as distal end 205 is reduced in diameter and thereby acts like a collet in a pin chuck. As shown in FIG. 3 when distal end 205 of guidewire gripping member 206 is not sufficiently advanced within tapered portion 207 of outer shaft 102 it does not grip guidewire 104. Fingers 211 may be radially spaced apart from, or slidingly engaged with the surface of guidewire 104 such that guidewire 104 remains slidable within catheter device 100. However, when distant end 205 of guidewire gripping member 206 is sufficiently advanced within tapered portion 207 of outer shaft 102, as shown in FIG. 4, fingers; 211 are forced to grip guidewire 104 in place with respect to catheter device 100. In such an engaged configuration, catheter device 100 and guidewire 104 are useable as a single mechanism, such that the additional support provided to guidewire 104 by catheter device 100 enables the combined components to be readily pushed through a difficult lesions such as a total occlusion or a CTO. Catheter device 100 and guidewire 104 may be selectively engaged and disengaged as may be desired during the medical procedure.

Figure 5:
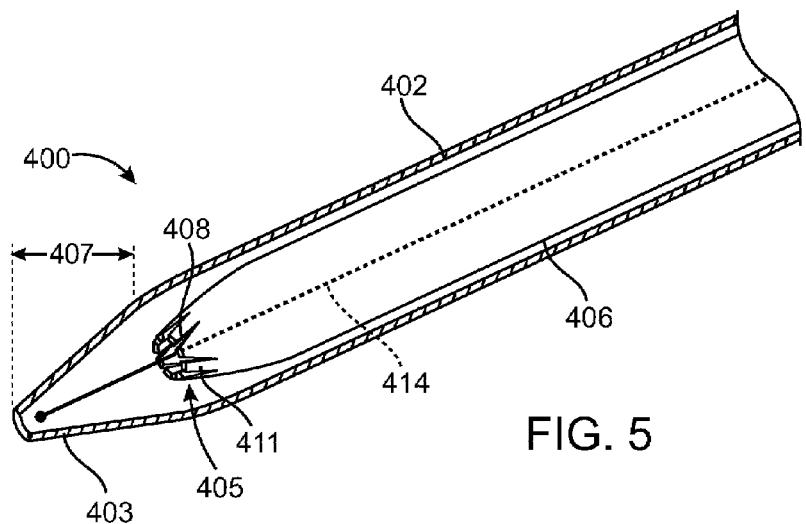
FIG. 5 illustrates a partial longitudinal sectional view of a distal portion of the catheter device of FIG. 1 in accordance with another embodiment of the present invention.

In an embodiment illustrated in FIG. 5, a steerable catheter or catheter device 400 includes an outer tubular member 402 and a guidewire gripping member 406 that are similar to those described in the previous embodiment. Distal end 405 of guidewire gripping member 406 includes a plurality of v-shaped slots 408 that define, a plurality of fingers 411, which are shown in a disengaged, open configuration in FIG 5. As distal end 405 is advanced within tapered portion 407 of outer tubular member 402 slots 208 between fingers 411 allow fingers 411 to converge as distal end 415 is reduced in diameter until fingers 411 make contact with and secure a guidewire (not-shown). Catheter device 400 includes a steering wire 414 attached to distal end 403 of outer tubular m-ember 402 and extending proximally to an actuation hub or handle (not shown), such as actuation hub 510 FIG. 7 to be described in further detail below. In this embodiment, steering wire 414 is positioned in the elongates annular space defined between a inner surface of outer tubular member 402 and an outer surface of guidewire gripping member 406.

Figure 6:
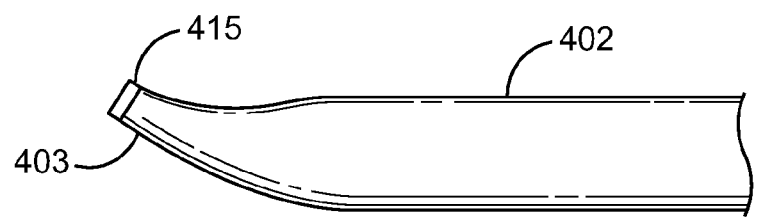
FIG. 6 illustrates a side view of the catheter device of FIG. 5 with its distal end in a deflected configuration.

When catheter device 400 is in the disengaged, open configuration such that distal end 405 of guidewire gripping member 406 is not in contact, or is in sliding contact with tapered portion 407 of outer tubular member 402, steering wire 414 may be retracted, or displaced proximally, to deflect or bend the distal tip of catheter device 400 from a straight configuration into a deflected configuration, for example, as shown in FIG. 6. The distal tip of catheter device 400 may then be secured in its deflected configuration by advancing guidewire gripping device 406 into contract with tapered portion 407 and, subsequently, into en engaged, gripping configuration with respect to the guidewire. In an embodiment, a radiopaque marker ring 415 may be mounted at a distal tip of catheter device 400 to aid in fluoroscopic observation of the device within a patient during an interventional procedure. In an embodiment, steering wire 406 may be secured to a metallic marker ring 415 by adhesive or by metal joining techniques such as soldering, brazing or welding.

In another embodiment (not shown), a wall of the outer tubular member of shaft may include a steering wire lumen or channel that accomodates sliding movement of the steering wire and separates the steering wire from the outer shaft lumen containing the guidewire gripping member. In various embodiments of the present invention, such a steering wire channel may extend along an entire length of the outer tubular member, or for some lesser length thereof.

Figure 7:
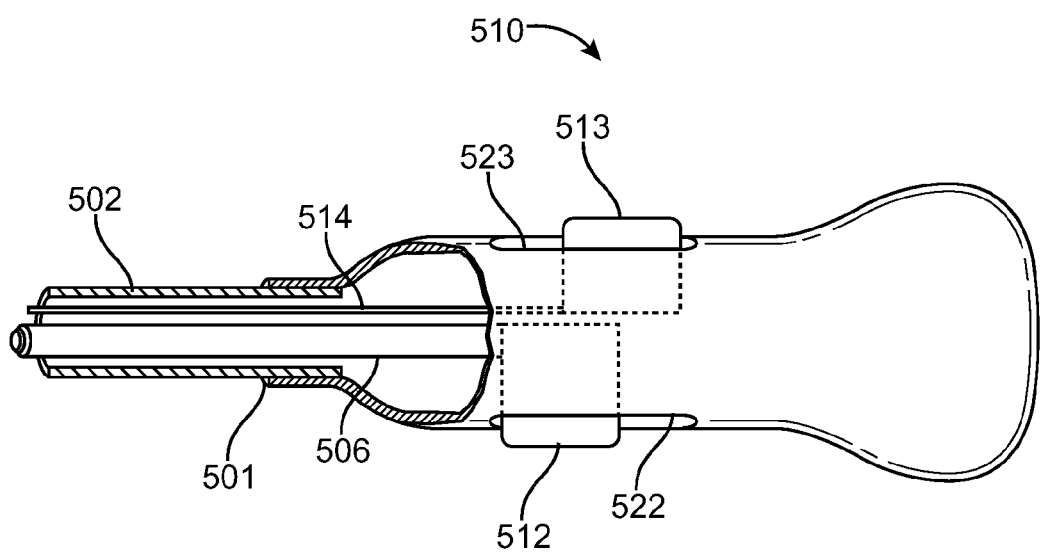
FIG. 7 illustrates an actuation hub for use with a catheter device in accordance with various embodiments of the present invention.

FIG. 7 illustrates an embodiment of an actuation hub 510 for use with a steerable catheter device in accordance with an embodiment of the present invention. A proximal end 501 of outer shaft 502 of the catheter device is attached at a distal end of actuation hub 510. A guidewire gripping member 506 and a steering wire 514 slidably extend within outer shaft 502 and provide the same functionality described with reference to the like components in the embodiment of FIG. 5. Actuation hub 510 includes two slidable actuation buttons or levers 512, 513 that are coupled to guidewire gripping member 506 and steering wire 514, respectively, and act as push-pull mechanism. Actuation button 512 may be attached at a distance from the proximal end of guidewire gripping member 506, which may extend proximally out of actuation hub 520 for insertion and withdrawal of a guidewire therein. Each actuation button 512, 513 are slidable within an actuation slot 522, 523 respectively.

Actuation slot 522 provides a limit to how far distally guidewire gripping member 506 may be pushed/advanced within outer shaft 502 to prevent an over-advancing the distal end of guidewire gripping member 506 that could cause over-stressing or unintentional bending of the tapered portion (not shown) at the distal end of outer shaft 502. In a similar manner, actuation slot 523 provides a limit to how far proximally steering wire 513 may be pulled to avoid breaking the wire and/or over-deflection of the distal end of the cathter device. In FIG. 7, actuation buttons 512, 513 of actuation hub 510 are positioned within slots 522, 523 respectively such that the catheter tip is deflected and guidewire gripping device 506 is fully advanced within outer shaft 502 to be engaged with a guidewire (not shown). Actuation buttons 512, 513 have pawls (not shown) for relesably engaging ratchet teeth (not shown) disposed along slots 522, 523 respectively to selectively lock actuation buttons 512, 513 in desired positions with respect to actuation hub 510. Such locking action frees the clinical's hands to manipulate catheter device 100 and guidewire 104 in engaged configuration, with or without tip 403 being held in a deflected configuration as shown in FIG. 6. Alternatively, actuation hub 510 may include other mechanism for releasbly holding guidewire gripping member 506 and/or steering wire 513 in a fixed axial position with respect to outer shaft 502, as will be understood by one of ordinary skill in the art of medical devices.

Outer shaft 102 of catheter device 100 is a long, hollow tube that is flexible enough to navigate the tortuous pathways of the cardiovascular system while being longitudinally incompressible enough to be pushed through the vasculature. Outer shaft 102 may include tubing made from a thermoplastic material, such as polyether block amide copolymer (PEBA), polyvinyl chloride, polyethylene, polyethylene terephthalate, polyamide, thermoplastic polyurethan (TPU), or a thermoset polymer such as polyimide, or a combination thereof. Distal tapered portion 207 may be thermoformed in the distal end of outer shaft 102. Alternatively, tapered portion 207 may be made as a separate element that is subsequently attached to outer shaft 1-2. Such a separate tapered portion 207 may be formed of metal, thermoplastic or thermoset polymer.

In an embodiment of the present invention, outer shaft 102 of catheter device 100 may be made from multilayer tubing having an inner layer, a reinforcing layer (not shown), and an outer layer or jacket. The inner layer may be manufactured of a high density polyethylen (HDPE) that provides good flexibility and movement of outer shaft 102 over guidewire gripping member 206. In another embodiment, the inner layer may be manufactured of a polyamide with a slippery coating for facilitating movement of guidewire gripping member 206 within outer shaft 102. Those of ordinary skill in the art may appreciate that any one of numerous low-friction biocompatible materials such as, for example, fluoropolymers (e.g., PTFE, PEP), polyolefins (e.g., polypropylene, high-density polyethylene), or polyamides, may be used as the inner layer of outer shaft 102. The reinforcing layer of outer shaft 102 is positioned between the inner layer and outer jacket of outer shaft 102.

The reinforcing layer may extend over the length of outer shaft 102, or for a lesser length thereof. In an embodiment, a braid at a distal tip of outer shaft 102 may reinforce conical/tapered portion 207 of distal end 103, which will retain an inner and outer diameter of distal end 103 when brought into contact with distal end 205 of guidewire gripping member 206. In various embodiments, the reinforcing layer may be formed by braiding multiple filaments or winding at least one filament over the inner layer or by applying a metal mesh over the inner layer, such as a wire or mesh made from 304 stainless steel or nitinol. Braided or wound filaments may comprise high-modules thermoplastic or thermo-set plastic materials, e.g., liquid crystal polymer (LCP), polyester, or aramid polymer e.g. poly-paraphenylene terephthalamide (Kevlar® from E.I. du Pont de Nemours and Company, Wilmington. Del., U.S.A.). Alternatively, braided or wound filaments may include metal such as tantalum, or a work-hardenable super alloy comprising nickle, cobalt, chromium and molybdenum. The outer jacket of outer shaft 102 covers the reinforcing layer, and in embodiments of the present invention, may be manufactured of a polyamide, such as a polyether block amide copolymer or nylon 66.

Guidewire gripping member 206 is manufactured from a thin-walled tubing that is flexible enough to navigate the tortuous pathways of the cardiovascular system while being longitudinally incompressible enough to allow distal end 205 of guidewire gripping member 206 to be advanced and longitudinally forced against the inside of tapered portion 207 of outer shaft 102 to contact and grip guidewire 104. In an embodiment, guidewire gripping member 206 may be made from a thin-walled polyimide tube. In another embodiment, the thin-walled tubing may be a co-extrusion having polylene, or a copolymer thereof, as an inner layer and a stiffer material, such as nylon as an outer layer to impart pushability to guidewire gripping member 206. Slots 208 are then cut within a distal end of the tubing to form gripping jaws or fingers 211, as described above.

Figure 8:
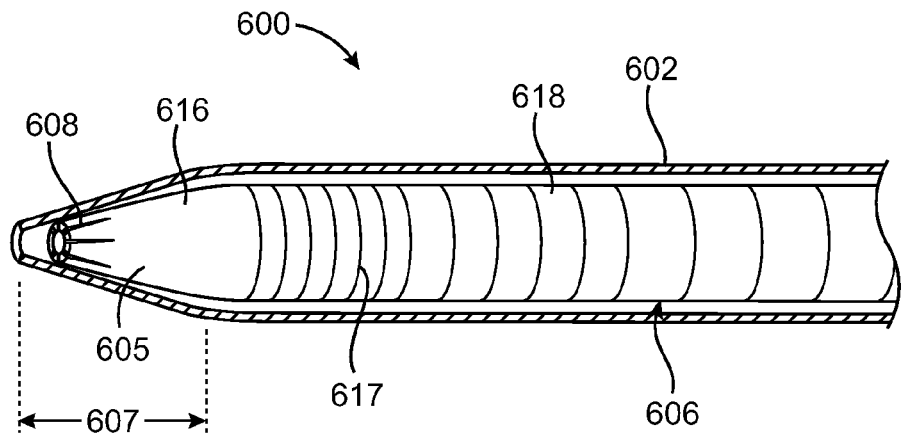
FIG. 8 illustrates a partial longitudinal sectional view of a distal portion of a catheter device in accordance with another embodiment of the present invention.

FIG. 8 illustrates a partial longitudinal sectional view of a distal section of a catheter device 600 in accordance with another embodiment of the present invention. Catheter device 600 includes an outer shaft 602 having a conical or tapered distal portion 607 similar to outer shaft 102 described in the embodiment of FIGS. 1 and 2. However in this embodiment guidewire gripping member 606 includes a collet 616 that is attached to a shaft 618. Collet 616 includes slots 608 in a distal end 605 thereof, and is made of a semi-rigid material, such as polyimide, for structural stability when advanced and compressed within tapered portion 607 of outer shaft 602. Shaft 618 is a thin-walled, tubular structure that extends within outer shaft 602 from collet 616 to all actuation hub (not shown). Shaft 618 provides a guidewire lumen for directing a guidewire (not shown) into collet 616. Shaft 618 includes a helical cut 617 into or through a wall thereof. Alternatively, shaft 618 may be an elongate coil spring. In an embodiment, the pitch or spacing between slits of helical cut 617 decreases as shaft 618 extends distally, such that shaft 618 increases in flexibility in a distal direction. Shaft 618 may be made from tubing of a metallic material, such as stainless steel, nitinol, or a cobalt-chromium superalloy. Such metallic tubing is commonly referred to as hypodermic tubing or a hypotube. Metallic tubing formed from other alloys, as disclosed in U.S. Pat. No. 6,168,571, which is incorporated by reference herein its entirety, may also be used in the tubing of the present invention.

Figure 9:
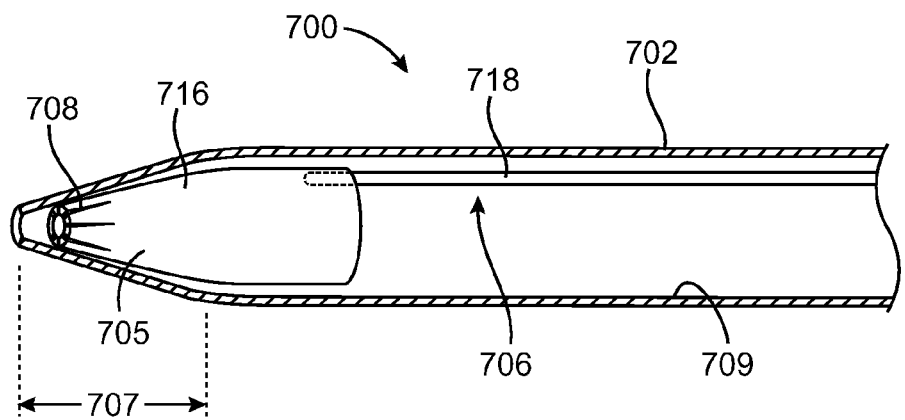
FIG. 9 illustrates a partial longitudinal sectional view of a distal portion of a catheter device in accordance with another embodiment of the present invention.

FIG. 9 illustrates at partial longitudinal sectional view, of a distal portion of a catheter device 700 in accordance with another embodiment of the presents invention. Catheter device 700 includes an outer shaft 702 having a conical or tapered distal portion 717 similar to outer shaft 102 described in the embodiment of FIGS. 1 and 2. In this embodiment, guidewire gripping member 706 includes a collet 716 that is attached to a shaft 718. Collet 716 includes slots 708 in a distal end 705 therof, and is made of a semi-rigid material, such as polyimide, for structural stability when advanced and compressed within tapered portion 707 of outer shaft 702. Shaft 718 is a long, flexible wire that has enough pushability, i.e., longitudinal stiffness, to allow distal end 705 of guidewire gripping member 706 to be advanced and forced against tapered portion 707 of outer shaft 702 to contact and grip a guidewire (not shown). Shaft component 718 extends within outer shaft 702 from collet 716 to an actuation hub (now shown). Shaft 718 may be a solid core wire made from a metal, such as nitinol, stainless steel, or coblat-chromium superalloy. In an embodiment of the present invention, shaft 718 may be tapered at its distal end proximate to where it attaches to collet 716 and/or may include one or more sections of different materials. Shaft 718 may be centerless-ground to have several diameters in its profile (not shown) in order to provide regions of different stiffness with gradual transitions there between in this embodiment, a guidewire is tracked through an interior of collet 716 and lumen 709 of outer shaft 702 to extend from a proximal end of catheter device 700.

While various embodiment according to the present invention have been described above, it should be understood that they have been presented by way of illustration and example only, and not limitation. It will be apparent to persons skilled in the relevant art than various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiments discussed herein, and of each reference cited herein, can be used in combination with the features of any other embodiment. All patents and publication discussed herein are incorporated by reference herein in their entirety.

What is claimed is:

1. A catheter device for selectively aiding a guidewire in crossing a lesion in a body vessel, the catheter device comprising:
    an elongate flexible outer tubular member that is capable of being navigated through a patient's vasculature to the lesion in the body vessel, the outer tubular member having a lumen extending from a proximal end to a distal end thereof, the distal end of the outer tubular member having a tapered portion wherein at least an inner diameter of the outer tubular member tapers toward the distal end; and
    a guidewire gripping member slidably disposed within the lumen of the outer tubular member, the guidewire gripping member having a guidewire lumen for slidably receiving a guidewire and a distal end with a plurality of longitudinal slots defining fingers therein,
    wherein a diameter of the distal end of the guidewire gripping member is reduced when the guidewire gripping member is advanced distally within the tapered portion of the outer tubular member such that the fingers of the guidewire gripping member grip the guidewire to thereby prevent movement of the guidewire relative to the catheter device.

2. The catheter device of claim 1, wherein the guidewire gripping member is an elongate inner tubular member.

3. The catheter device of claim 2, wherein the inner tubular member comprises polyimide.

4. The catheter device of claim 2, wherein the inner tubular member includes a helical cut into or through a wall thereof.

5. The catheter device of claim 1, wherein the guidewire gripping member includes a collet attached to a shaft and the collet is the distal end of the guidewire gripping member having the longitudinal slots therein.

6. The catheter device of claim 5, wherein the collet comprises polymide and the shaft is a metallic wire.

7. The catheter device of claim 5, wherein the collet comprises polyimde and the shaft is a hypotube.

8. The catheter device if claim 1 further comprising:
    a hub fixed at a proximal end of the outer tubular member, the hub having an actuation mechanism for advancing and retracting the guidewire gripping member within the outer tubular member.

9. The catheter device of claim 8, wherein the actuation mechanism includes a slidable button coupled to a proximal end of the guidewire gripping device that cooperates with an actuation slot in the hub for limiting the advancement and retraction of the guidewire gripping device.

10. The catheter device of claim 1 further comprising:
    a steering wire for deflecting a distal end of the catheter device the steering wire having a distal end attached to the distal end of the outer tubular member and a proximal end positioned at a proximal end of the catheter device.

11. The catheter device of claim 10, wherein a length of the steering wire is slidably disposed within the lumen of the other tubular member.

12. The catheter device of claim 10, further comprising:
    a hub disposed at the proximal end of the catheter device, the hub having an actuation mechanism for advancing and retracting the steering wire within the outer tubular member.

13. The catheter device of claim 12, wherein the actuation mechanism includes a slidable button coupled to the proximal end of the steering wire, the button cooperating with an actuation slot in the hub for limiting the advancement and retraction of the steering wire.

14. The catheter device of claim 10, further comprising:
    a hub disposed at the proximal end of the catheter device, the hub having a first actuation mechanism for advancing and retracting the steering wire within the outer tubular member and a second actuation mechanism for advancing and retracting the guidewire gripping member within the outer tubular member.

15. The catheter device of claim 14, wherein the first actuation mechanism includes a first slidable button coupled to the proximal end of the steering wire, the button cooperating with a first actuation slot in the hub for limiting the advancement and retraction of the steering wire.

16. The catheter device of claim 15, wherein the second actuation mechanism includes a second slidable button coupled to a proximal end of the guidewire gripping member, the button cooperating with a second actuation slot in the hub for limiting the advancement and retraction of the guidewire gripping member.

17. A method of crossing a lesion in a body vessel, the method comprising:
   advancing a guidewire through a patient's vasculature to position a distal end proximate to the lesion;
   receiving a catheter device having an elongate flexible outer shaft with a tapered distal portion and a guidewire gripping member slidably disposed within the outer shaft, wherein the guidewire gripping member includes a guidewire lumen and a distal end having longitudinal slots defining fingers therein;
   tracking the catheter device over the indwelling guidewire until the tapered distal portion of the outer shaft is positioned proximate to the distal end of the guidewire;
   distally advancing the guidewire gripping member relative to the outer shaft of the catheter device such that the fingers on the distal end of the guidewire gripping member converge within the tapered distal portion of the outer shaft into gripping engagement with the guidewire to secure the catheter device to the guidewire; and
   pushing the combined catheter device and guidewire such that the tapered distal portion of the outer shaft that surrounds the guidewire gripping member passes through the lesion.

18. The method of claim 17, further comprising, after pushing the combined catheter device and guidewire through the lesion:
   proximally retracting the guidewire gripping member relative to the outer shaft of the catheter device, such that the fingers on the distal end of the guidewire gripping member spread into disengagement with the guidewire to permit the catheter device to slide along the guidewire.

19. The method of claim 17, wherein the catheter device further includes a steering wire attached to a distal end of the catheter device.

20. The method of claim 19, further comprising:
   retracting the steering wire to deflect the distal end of the catheter device prior to the step of distally advancing the guidewire gripping member relative to the outer shaft of the catheter device.

21. The method of claim 20, further comprising:
   steering the combined catheter device and guidewire gripping member to a crossing point in the lesion prior to the step of pushing the combined catheter device and guidewire gripping member through the lesion.

* * * * *

UNITED STATES PATENT AND TRADEMARK OFFICE
CERTIFICATE OF CORRECTION

PATENT NO. : 7,682,365 B2  Page 1 of 1
APPLICATION NO. : 11/559043
DATED : March 23, 2010
INVENTOR(S) : Terry Guinan It is certified that error appears in the above-identified patent and that said Letters Patent is hereby corrected as shown below:

Column 8, line 31, claim 7 "comprises polyimde and the shaft is a hypotube"
should be changed to --comprises polyimide and the shaft is a hypotube--

Column 8, line 44, claim 10 "device the steering wire having a distal end attached to"
should be changed to --device, the steering wire having a distal end attached to--

Signed and Sealed this

Nineteenth Day of October, 2010

David J. Kappos
*Director of the United States Patent and Trademark Office*